(12) United States Patent
Hagiya

(10) Patent No.: US 7,554,000 B2
(45) Date of Patent: Jun. 30, 2009

(54) PROCESS FOR PRODUCING BIARYL COMPOUND

(75) Inventor: Koji Hagiya, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 472 days.

(21) Appl. No.: 10/502,619

(22) PCT Filed: Jan. 15, 2003

(86) PCT No.: PCT/JP03/00245

§ 371 (c)(1),
(2), (4) Date: Jul. 27, 2004

(87) PCT Pub. No.: WO03/066546

PCT Pub. Date: Aug. 14, 2003

(65) Prior Publication Data

US 2005/0096471 A1 May 5, 2005

(30) Foreign Application Priority Data

Feb. 5, 2002 (JP) ............................. 2002-027907
Mar. 7, 2002 (JP) ............................. 2002-061608
Sep. 4, 2002 (JP) ............................. 2002-258584

(51) Int. Cl.
*C07C 15/14* (2006.01)
(52) U.S. Cl. .................................................... 585/425
(58) Field of Classification Search ................ 585/425; 546/257, 517; 548/517
See application file for complete search history.

(56) References Cited

FOREIGN PATENT DOCUMENTS

JP        55-133367 A    10/1980
JP        2002-53569 A    2/2002

OTHER PUBLICATIONS

Rosenberg et al ,Tetrahedron Letters vol. 21, p. 4141-4144, 1980.*
Gessner G Hawley, the Condensed Chemical Dictionary, 8th ed, 1975, p. 455-456.*
Firouzabadi, H. et al., Barium Ferrate Monohydrate BaFeo$_4$ H$_2$O, a Useful Oxidant for the Oxidation of Organic Compounds under Aprotic Conditions., Bull. Chem. Soc. Jpn., vol. 61, No. 6, (1988), pp. 2185 to 2189, particularly, p. 2187, table 3, No. 9.
Hardie, R.L. and Thomson, R.H., "the Oxidation of Phenylhydrazine", *J. Chem Soc.*, 2512-2518 (1957).
Demir, A. et al., "Manganese (III) acetate-mediated oxidative coupling of phenylhydrazines with benzene: a novel method for biaryl coupling", *J. Chem. Soc.*, Perkin Trans. 1, 3042-3045 (2001).
Firouzabadi, J. et al., "Barium Ferrate Monohydrate BaFeO$_4$ H$_2$O, a Useful Oxidant for the Oxidation of Organic Compounds under Aprotic Conditions", *Bull. Chem. Soc. Jpn.*, 61, 2185-2189 (1988).
Crank, G. et al., "The Reactions of Superoxide Ion with Arylhydrazines", *Aust. J. Chem.*, 37, 2499-2507 (1984).
"Oxidation of Phenylhydrazine in an Alkaline Solution", Justus Liebigs, *Ann. Chem.*, vol. 190, 101-102 (1878).
"Oxidation of Phenylhydrazine by Mercury Oxide", Justus Liebigs, *Ann. Chem.*, vol. 199, 332 (1879).
Aylward, J.B., "Oxidation of Hydrazine Derivatives. Part 1. Oxidation of Phenyl-hydrazine with Lead Tetra-acetate", *J. Chem. Soc. (C)*, 1663-1665 (1969).
Coupling Reactions Between sp$^2$ Carbon Centers, *Comprehensive Organic Synthesis*, 3, 499-520 (1991).
Tale, R.H., "Novel Synthesis of 2-Arylbenzothiazoles Mediated by Ceric Ammonium Nitrate", *Organic Letters*, vol. 4, No. 10, 1641-1642 (2002).
Chang, Yi-Hua et al., "A General and Efficient Synthesis of 2-Phenylbenzothiazoles from Diphenyl Disulfides", *Synthetic Communications*, 23(5), 663-670 (1993).
Chang, Junbiao, et al., "Synthesis of 2-arylbenzoxazoles via DDQ promoted oxidative cyclization of phenolic Schiff bases—a solution-phase strategy for library synthesis", *Tetrahedron Letters*, 43, 951-954 (2002).
Shi, Dong-Fang et al., "Antitumor Benzothiazoles. 3.[1] Synthesis of 2-(4-Aminophenyl)benzothiazoles and Evaluation of Their Activities against Breast Cancer Cell Lines in Vitro and in Vivo", *J. Med. Chem.*, 39, 3375-3384 (1996).

* cited by examiner

*Primary Examiner*—Taylor Victor Oh
(74) *Attorney, Agent, or Firm*—Birch, Stewart, Kolasch & Birch, LLP

(57) ABSTRACT

A process for producing a biaryl compound, characterized by reacting an arylhydrazine compound, hydrogen peroxide and an aryl compound. When the reaction is conducted in the presence of a given metal or a compound of the metal or in the presence of a metal oxide obtained by reacting the given metal or a compound of the metal with hydrogen peroxide, then the yield of the biaryl compound is improved.

6 Claims, No Drawings

PROCESS FOR PRODUCING BIARYL COMPOUND

TECHNICAL FIELD

The present invention relates to a process for producing a biaryl compound.

BACKGROUND ART

A biaryl compound is an extremely important compound as various chemical products and intermediates for synthesis of them. It is generally known that a biaryl compound can be produced by Suzuki coupling reaction using aryl boric acid, a reaction using a nickel catalyst and a Grignard reagent, Ullmann reaction using aryl iodide, or the like (e.g. Comprehensive Organic Synthesis, 3, 499 (1991) etc.). However, all these methods use an expensive reagent, ligand or catalyst and, therefore, further improvement has been desired from an industrial point of view.

On the other hand, as a process for producing a biaryl compound without an expensive reagent, ligand or catalyst such as the above-mentioned reagent, ligand or catalyst, there was proposed a method comprising reaction of an arylhydrazine compound, an oxidizing agent and an aryl compound. For example, methods using, as an oxidizing agent, (1) silver oxide (J. Chem. Soc., 2512 (1957)), (2) manganese acetate (J. Chem. Soc. Perkin Trans. 1, 3042(2001)), (3) mercury oxide (Liebigs Ann. Chem., 199, 332(1879)), (4) barium ferrate (Bull. Chem. Soc. Jpn., 61, 2185(1988)), (5) lead acetate (J. Chem. Soc. (C), 1663(1969)) and (6) potassium superoxide (Aust. J. Chem., 37, 2499 (1984)) respectively were reported. However, all the above-mentioned oxidizing agents are relatively expensive and moreover, may be toxic or be difficult to handle after reaction. Therefore, development of an industrially more advantageous method has been desired.

DISCLOSURE OF THE INVENTION

Under such circumstances, the present inventor intensively studied a process of industrially and more advantageously producing a biaryl compound and as a result, found that a biaryl compound can be produced from an arylhydrazine compound or an arylhydrazine compound and an aryl compound by using hydrogen peroxide, which is inexpensive, easy to use and converted into harmless water after reaction, that is, a clean and excellent oxidizing agent. Further, the present inventor found that the yield of a biaryl compound can be improved by performing the reaction in the presence of at least one species selected from the group consisting of the following groups (A) and (B):

(A) a Group Va element metal or a compound thereof, a Group VIa element metal or a compound thereof, a Group VIIa element metal or a compound thereof and a Group VIIIa element metal or a compound thereof, (B) a Group Va element metal oxide, a Group VIa element metal oxide, a Group VIIa element metal oxide and a Group VIIIa element metal oxide obtained by reacting the metal or the metal compound of the group (A) with hydrogen peroxide, and finally completed the present invention.

That is, the present invention provides:

(1) a process for producing a biaryl compound, which comprises reacting an arylhydrazine compound, hydrogen peroxide and an aryl compound, (2) a process for producing a biaryl compound, wherein the reaction as described in the above (1) is performed in the presence of at least one species selected from the group consisting of the following groups (A) and (B):

(A) a Group Va element metal or a compound thereof, a Group VIa element metal or a compound thereof, a Group VIIa element metal or a compound thereof and a Group VIIIa element metal or a compound thereof, (B) a Group Va element metal oxide, a Group VIa element metal oxide, a Group. VIIa element metal oxide and a Group VIIIa element metal oxide obtained by reacting the metal or the metal compound of the group (A) with hydrogen peroxide, (3) a process for producing a biaryl compound, which comprises reacting an arylhydrazine compound with hydrogen peroxide, and (4) a process for producing a biaryl compound, wherein the reaction as described in the above (3) is performed in the presence of at least one species selected from the group consisting of the above-mentioned groups (A) and (B).

MODE FOR CARRYING OUT THE INVENTION

First, a process for producing a biaryl compound by reacting an arylhydrazine compound, hydrogen peroxide and an aryl compound, and a method of performing the aforementioned reaction in the presence of at least one selected from the group consisting of the aforementioned groups (A) and (B) will be explained.

The arylhydrazine compound may be a compound in which at least one hydrazino group is bound to an aromatic ring (e.g. a benzene ring or a naphthalene ring), a heteroaromatic ring (e.g. a pyridine ring, a thiazole ring or an oxazole ring) or a fused heteroaromatic ring (e.g. benzothiazole, benzoxazole, quinoline or isoquinoline). The arylhydrazine compound may have a substituent other than a hydrazino group on the aromatic ring or the heteroaromatic ring.

Such arylhydrazine compound includes an arylhydrazine compound represented by the formula (1):

$$Ar-NHNH_2 \qquad (1)$$

wherein Ar represents an aromatic group such as a phenyl group or a naphthyl group, or a heteroaromatic group such as a pyridyl group, a thiazolyl group or an oxazolyl group (e.g. benzothiazole, benzoxazole, quinoline, isoquinoline, etc.).

A substituent of the arylhydrazine compound (including the arylhydrazine compound of the aforementioned formula (1)) will be explained below.

The substituent other than a hydrazino group includes a substituted or unsubstituted alkyl group, a substituted or unsubstituted alkoxy group, a substituted or unsubstituted alkoxycarbonyl group, a substituted or unsubstituted aryl group, a substituted or unsubstituted aryloxy group, a substituted or unsubstituted aryloxycarbonyl group, a substituted or unsubstituted aralkyl group, a substituted or unsubstituted aralkyloxy group, a substituted or unsubstituted aralkyloxycarbonyl group, a substituted or unsubstituted acyl group, a halogen atom, a carboxyl group, a sulfo group ($-SO_3H$), a sulfonamido group, a sulfonic acid (aryl or alkyl) ester group, a sulfonyl group, a cyano group, a hydroxyl group, a nitro group, an amino group and an amido group.

Among these substituents, adjacent substituents may be taken together to form a part of a ring structure.

The halogen atom includes a fluorine atom, a chlorine atom and a bromine atom.

The alkyl group of the substituted or unsubstituted alkyl group, the substituted or unsubstituted alkoxy group, and the substituted or unsubstituted alkoxycarobonyl group includes straight, branched or cyclic alkyl groups having 1 to 20 carbon atoms, such as a methyl group, an ethyl group, a n-propyl group, an isopropyl group, a n-butyl group, an isobutyl group, a sec-butyl group, a tert-butyl group, a n-pentyl group, a n-hexyl group, a n-heptyl group, a n-octyl group, a n-nonyl group, a n-decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a 2,2-dimethylcyclopropyl group, a cyclopentyl group, a cyclohexyl group or a menthyl group. In the present invention, unless otherwise indicated, an alkyl group has the aforementioned meaning.

The aryl group of the substituted or unsubstituted aryl group, the substituted or unsubstituted aryloxy group and the substituted or unsubstituted aryloxycarbonyl group includes a phenyl group, a naphthyl group and a biphenyl group. In the present invention, unless otherwise indicated, an aryl group has the aforementioned meaning.

The aralkyl group of the substituted or unsubstituted aralkyl group, the substituted or unsubstituted aralkyloxy group and the substituted or unsubstituted aralkyloxycarbonyl group includes groups formed by binding of the aforementioned alkyl group and the aryl group. In the present invention, unless otherwise indicated, an aralkyl group has the aforementioned meaning.

The acyl group of the substituted or unsubstitued acyl group includes groups formed by binding of the aforementioned alkyl group or aryl group and a carbonyl group. In the present invention, unless otherwise indicated, an acyl group has the aforementioned meaning.

The substituted alkyl group includes alkyl groups substituted with substituent(s) selected from an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group ($-SO_3H$), a sulfonamido group, a sulfonic acid (aryl or alkyl) ester group, a sulfonyl group, a cyano group, a hydroxyl group, a nitro group, a amino group and an amido group.

The substituted aryl group includes aryl groups substituted with substituent(s) selected from an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group ($-SO_3H$), a sulfonamido group, a sulfonic acid (aryl or alkyl) ester group, a sulfonyl group, a cyano group, a hydroxyl group, a nitro group, an amino group and an amido group.

The substituted aralkyl group includes aralkyl groups substituted with substituent(s) selected from an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group ($-SO_3H$), a sulfonamido group, a sulfonic acid (aryl or alkyl) ester group, a sulfonyl group, a cyano group, a hydroxyl group, a nitro group, an amino group and an amido group.

The substituted alkyl group includes a bromomethyl group, a chloromethyl group, a fluoromethyl group, a trifluoromethyl group, a methoxymethyl group, an ethoxymethyl group, a methoxyethyl group and a methoxymethylcarbonyl group.

The alkoxy group specifically includes straight, branched or cyclic alkoxy groups having 1 to 20 carbon atoms, such as a methoxy group, an ethoxy group, a n-propoxy group, an isopropoxy group, a n-butoxy group, an isobutoxy group, a sec-butoxy group, a tert-butoxy group, a n-pentyloxy group, a n-heptyloxy group, a n-octyloxy group, a n-nonyloxy group, a n-decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, an eicosyloxy group, a cyclopropyloxy group, a 2,2-dimethylcyclopropyloxy group, a cyclopentyloxy group, a cyclohexyloxy group and a menthyloxy group.

The substituted alkoxy group includes, for example, alkoxy groups substituted with the aforementioned halogen atom, alkoxy, aryloxy, aralkyloxy, acyl, alkoxycarbonyl, aryloxycarbonyl, aralkyloxycarbonyl or carboxyl. Specific examples thereof include a chloromethoxy group, a fluoromethoxy group, a trifluoromethoxy group, a methoxymethoxy group, an ethoxymethoxy group and a methoxyethoxy group.

The substituted aryl group specifically includes a 2-methylphenyl group, a 4-chlorophenyl group, a 4-methylphenyl group, a 4-methoxyphenyl group and a 3-phenoxyphenyl group.

The substituted or unsubstituted aryloxy group specifically includes a phenoxy group, a 2-methylphenoxy group, a 4-chlorophenoxy group, a 4-methylphenoxy group, a 4-methoxyphenoxy group and a 3-phenoxyphenoxy group.

The substituted or unsubstituted aralkyl group includes a benzyl group and a phenylethyl group.

The substituted or unsubstituted aralkyloxy group includes a benzyloxy group.

The substituted or unsubstituted acyl group includes a methylcarbonyl group, an ethylcarbonyl group, a phenylcarbonyl group and a benzylcarbonyl group.

The substituted or unsubstituted alkoxycarbonyl group, the substituted or unsubstituted aryloxycarbonyl group and the substituted or unsubstituted aralkyloxycarbonyl group include a methoxycarbonyl group, an ethoxycarbonyl group, a phenoxycarbonyl group and a benzyloxycarbonyl group, respectively.

The arylhydrazine compound includes a compound of the formula (1) wherein Ar is benzothiazole, which is 2-hydrazinobenzothiazole represented by the following formula (1'):

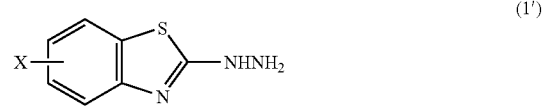

(1')

wherein X represents the same group as the substituent of Ar.

The arylhydrazine compounds represented by Formulas (1) and (1') include phenylhydrazine, 2-fluorophenylhydrazine, 3-fluorophenylhydrazine, 4-fluorophenylhydrazine, 2-chlorophenylhydrazine, 3-chlorophenylhydrazine, 4-chlorophenylhydrazine, 2-bromophenylhydrazine, 3-bromophenylhydrazine, 4-bromophenylhydrazine, 3-cyanophenylhydrazine, 4-cyanophenylhydrazine, 2-methoxycarbonylphenylhydrazine, 2-n-butoxycarbonylphenylhydrazine, 3-methoxycarbonylphenylhydrazine, 4-methoxycarbonylphenylhydrazine, 2-nitrophenylhydrazine, 3-nitrophenylhydrazine, 4-nitrophenylhydrazine, 2-methylphenylhydrazine, 3-methylphenylhydrazine, 4-methylphenylhydrazine, 2-methoxyphenylhydrazine, 3-methoxyphenylhydrazine, 4-methoxyphenylhydrazine, 2-trifluoromethylphenylhydrazine, 3-trifluoromethylphenylhydrazine, 4-trifluoromethylphenylhydrazine, 2-hydroxyphenylhydrazine, 3-hydroxyphenylhydrazine, 4-hydroxyphenylhydrazine, 2-carboxyphenylhydrazine, 3-carboxyphenylhydrazine, 4-carboxyphenylhydrazine, 4-(chloromethyl)phenylhydrazine, 2-sulfophenylhydrazine, 3-sulfophenylhydrazine, 4-sulfophenylhydrazine, 4-sulfonamidophenylhydrazine, ethyl 4-sulfonate phenylhydrazine, 3-methylsulfonphenylhydrazine, 2,3-dimethylphenylhydrazine, 3,5-dimethylphenylhydrazine, 3,5-trifluoromethylphenylhydrazine, 3,5-dinitrophenylhydrazine, 2,4-dinitrophenylhydrazine, 2,4-dichlorophenylhydrazine, 2,6-diethylphenylhydrazine, 2,5-difluorophenylhydrazine, 3,4-difluorophenylhydrazine, 2,4-difluorophenylhydrazine, 3,5-difluorophenylhydrazine, 3-chloro-4-fluorophenylhydrazine, 2-chloro-4-methylphenylhydrazine, 2-carboxy-3-chlorophenylhydrazine, 2-methoxycarbonyl-3-chlorophenylhydrazine, 4-cyano-2-chlorophenylhydrazine, 4-methyl-3-(chloromethyl)phenylhydrazine, 4-methyl-3-(bromomethyl)phenylhydrazine, 4-methyl-3-(methoxymethylcarbonyl)phenylhydrazine, 4-methyl-3-(carbamoylmethyl)phenylhydrazine, 4-methyl-3-cyanophenylhydrazine, 4-methyl-3-acetylphenylhydrazine, 3-sulfonamido-2-acetylaminophenylhydrazine, 2,3,5-trichlorophenylhydrazine, 3,4,5-trichlorophenylhydrazine, 2,4-difluoro-5-nitrophenylhydrazine, 2,3,5,6-tetrafluorophenylhydrazine, 2,3,4,5,6-pentafluorophenylhydrazine, 2-benzylphenylhydrazine, 3-benzyloxyphenylhydrazine, 4-benzyloxyphenylhydrazine, 2-aminophenylhydrazine, 3-aminophenylhydrazine, 4-aminophenylhydrazine, 1-naphthylhydrazine, 2-naphthylhydrazine, 4-hydrazino-1,8-naphthalic acid anhydride, diethyl 2-methyl-2-((3'-fluoro-4'-hydrazino)phenyl)malonate, 4-chloro-3-hydroxy-2-fluorophenylhydrazine, 4-trifluoromethyl-2,6-dichlorophenylhydrazine, 5-methoxy-2,4-dichlorophenylhydrazine, 2-hydrazinopyridine, 6-bromo-2-hydrazinopyridine, 2-hydrazinopyrimidine, 4-trifluoromethyl-2-hydrazinopyrimidine, 2-ethoxy-4-fluoro-6-hydrazinopyrimidine, 2,4-dimethoxy-6-hydrazinopyrimidine, 2-hydrazinoquinoline, 4-nitro-2-hydrazinoquinoline, 2-hydrazinobenzothiazole, 2-hydrazinobenzoxazole, 2-hydrazino-4-methylbenzothiazole, 2-hydrazino-5-methylbenzothiazole, 2-hydrazino-6-methylbenzothiazole, 2-hydrazino-7-methylbenzothiazole, 2-hydrazino-4-ethylbenzothiazole, 2-hydrazino-5-isopropylbenzoxazole, 2-hydrazino-4-methoxybenzothiazole, 2-hydrazino-5-methoxybenzoxazole, 2-hydrazino-6-methoxybenzothiazole, 2-hydrazino-7-methoxybenzothiazole, 2-hydrazino-5,7-dimethoxybenzothiazole, 2-hydrazino-4,6-dimethoxybenzothiazole, 2-hydrazino-5,6-dimethoxybenzothiazole, 2-hydrazino-4-ethoxybenzothiazole, 2-hydrazino-5-benzyloxybenzothiazole, 2-hydrazino-7-benzyloxybenzothiazole, 2-hydrazino-4-chlorobenzothiazole, 2-hydrazino-5-chlorobenzothiazole, 2-hydrazino-6-chlorobenzoxazole, 2-hydrazino-4-fluorobenzothiazole, 2-hydrazino-5-fluorobenzoxazole, 2-hydrazino-6-fluorobenzothiazole, 2-hydrazino-5,7-dichlorobenzothiazole, 2-hydrazino-4,6-dichlorobenzothiazole, 2-hydrazino-5,6-dichlorobenzoxazole, 2-hydrazino-5,7-difluorobenzothiazole, 2-hydrazino-4,6-difluorobenzothiazole, 2-hydrazino-5,6-difluorobenzoxazole, 2-hydrazino-5-(2-methoxyethylcarbonyl)benzothiazole, 2-hydrazino-6-bromobenzothiazole, 2-hydrazino-5-trifluoromethylbenzothiazole, 2-hydrazino-6-trifluoromethylbenzoxazole, 2-hydrazino-5-cyanobenzothiazole, 2-hydrazino-6-cyanobenzoxazole, 2-hydrazino-5-nitrobenzoxazole and 2-hydrazino-6-nitrobenzothiazole.

Such arylhydrazine compounds may be addition salts with an acid such as hydrochloric acid, sulfuric acid or the like.

Hydrogen peroxide is usually used as a solution in water. Of course, a solution of hydrogen peroxide in an organic solvent may be used. The concentration of Hydrogen peroxide in the solution of hydrogen peroxide in water or an organic solvent is not particularly limited. However, in view of volume efficiency, safety and the like, it is practically 1 to 60% by weight. As the solution of hydrogen peroxide in water, a commercially available hydrogen peroxide solution may be usually used as it is or after, if necessary, adjusting the concentration by dilution or concentration. The solution of hydrogen peroxide in an organic solvent may be prepared, for example, by extracting the solution of hydrogen peroxide in water with an organic solvent or by distilling the solution of hydrogen peroxide in water in the presence of an organic solvent.

The amount used of hydrogen peroxide is usually 1 mol or more per 1 mol of the arylhydrazine compound and there is no upper limit in particular. However, in view of economy, the amount used of hydrogen peroxide is practically 10 mol or less per 1 mol of the arylhydrazine compound.

The aryl compound is not particularly limited as long as it is a compound having an aromatic ring such as a benzene ring or a naphthalene ring, or a heteroaromatic ring such as a pyridine ring, and having at least one hydrogen atom on the aromatic ring or the heteroaromatic ring. The aromatic ring or the heteroaromatic ring may be substituted. Such a substituent includes the aforementioned halogen atom, the aforementioned substituted or unsubstituted alkyl group, the aforementioned substituted or unsubstituted alkoxy group, the aforementioned substituted or unsubstituted aryl group, the aforementioned substituted or unsubstituted aryloxy group, the aforementioned substituted or unsubstituted aralkyl group, the aforementioned substituted or unsubstituted aralkyloxy group, the substituted or unsubstituted acyl group, the aforementioned substituted or unsubstituted carboalkoxy group, the aforementioned substituted or unsubstituted carboaryloxy group, the aforementioned substituted or unsubstituted carboaralkyloxy, a carboxyl group, a sulfo group, a cyano group, a hydroxyl group, a nitro group and an amino group. Alternatively, adjacent substituents of these substituents may be taken together to form a ring structure.

Such aryl compound includes a compound represented by the formula (2):

$$Ar' \quad (2)$$

wherein Ar' is a substituted or unsubstituted aromatic group or a substituted or unsubstituted heteroaromatic group, and has at least one hydrogen atom bound to the aforementioned group. The substituent is as defined above.

Specific examples of the aryl compound include benzene, toluene, xylene, fluorobenzene, 1,2-difluorobenzene, 1,4-difluorobenzene, chlorobenzene, 1,4-dichlorobenzene, 1,4-dibromobenzene, 1,3-dimethoxybenzene, 1,4-dimethoxybenzene, 1,3,5-trichlorobenzene, bromobenzene, 1,4-dibromobenzene, cyanobenzene, 1,4-dicyanobenzene, 1-cyano-4-chlorobenzene, benzoic acid, methyl benzoate, terephthalic acid, dimethyl terephthalate, methyl 4-tert-butylbenzoate, aniline, nitrobenzene, 1,4-diaminobenzene, methoxybenzene, phenol, m-cresol, p-cresol, benzenesulfonic acid, p-toluenesulfonic acid, acetophenone, benzophenone, naphthalene, anthracene, pyrene, pyridine, quinoline and isoquinoline.

If the amount used of the aryl compound is not enough, self-coupling reaction of the arylhydrazine compound proceeds easily. Therefore, the amount used of the aryl compound is usually 10 mol or more per 1 mol of the arylhydrazine compound and there is no upper limit in particular. For example, if the aryl compound is in liquid form under reaction condition, a greatly excessive amount of the aryl compound may be used both as a reaction material and a solvent.

The reaction between the arylhydrazine compound, hydrogen peroxide and the aryl compound is usually performed in a solvent which is inert to the reaction. Such a solvent includes ether solvents such as diethyl ether, methyl tert-butyl ether or tetrahydrofuran, ester solvents such as ethyl acetate, nitrile solvents such as acetonitrile or propionitrile, and aliphatic hydrocarbon solvents such as cyclohexane or n-heptane. The amount used of such a solvent is not particularly limited, but in view of volume efficiency and the like, it is practically 100 parts by weight or less per 1 part by weight of the arylhydrazine compound. Alternatively, as described above, if the aryl compound is in liquid form under reaction condition, it may be used as a solvent.

If the reaction temperature is too low, the reaction hardly proceeds and, if the reaction temperature is too high, side reaction such as degradation of the starting material arylhydrazine compound or the produced biaryl compound may proceed. Therefore, the practical reaction temperature is in a range of 0° C. to 200° C.

The reaction between the arylhydrazine compound, hydrogen peroxide and the aryl compound is usually performed by contacting or mixing the three compounds. The order of mixing them is not particularly limited, but, preferably, the arylhydrazine compound is added to a mixture of hydrogen peroxide and the aryl compound.

The reaction may be performed under normal pressure, or may be performed under increased pressure. In addition, progression of the reaction can be confirmed by a conventional analysis means such as gas chromatography, high performance liquid chromatography, thin layer chromatography, NMR and IR.

In this reaction, since water is produced as a by-product as the reaction proceeds, it is preferable that the reaction is performed while removing water present in the reaction system or the reaction is performed in the presence of a phase transfer catalyst. A method of performing the reaction while removing water present in a reaction system includes a method comprising coexistence of a dehydrating agent such as anhydrous magnesium sulfate, anhydrous sodium sulfate, anhydrous calcium chloride or metaboric acid in a reaction system, for example, a method using an azeotropic dehydrating apparatus.

The phase transfer catalyst is not particularly limited as long as it has phase transfer ability, and examples thereof include a quaternary ammonium salt, an amine N-oxide compound, a quaternary phosphonium salt, a crown ether compound and a polyethylene glycol compound. The quaternary ammonium salt or the amine N-oxide compound is preferable.

The quaternary ammonium salt includes quaternary ammonium chloride compounds such as trioctylmethylammonium chloride, trioctylethylammonium chloride, dilauryldimethylammonium chloride, lauryltrimethylammonium chloride, stearyltrimethylammonium chloride, lauryldimethylbenzylammonium chloride, tricaprylmethylammonium chloride, tridecylmethylammonium chloride, trihexylmethylammonium chloride, tridecylmethylammonium chloride, tetrabutylammonium chloride, benzyltrimethylammonium chloride, benzyltriethylammonium chloride, N-laurylpyridinium chloride, N-cetylpyridinium chloride or N-laurylpicolinium chloride, quaternary ammonium bromide compounds in which the chlorine ion constituting the above quaternary ammonium chloride compound is substituted with a bromine ion, quaternary ammonium iodide compounds in which the chlorine ion constituting the above quaternary ammonium chloride compound is substituted with an iodine ion, quaternary ammonium sulfite salts in which the chlorine ion constituting the above quaternary ammonium chloride compound is substituted with a sulfite ion, quaternary ammonium sulfate salts in which the chlorine ion constituting the above quaternary ammonium chloride compound is substituted with a sulfate ion and quaternary ammonium hydrogen sulfate salts in which the chlorine ion constituting the above quaternary ammonium chloride compound is substituted with a hydrogen sulfate ion.

The amine N-oxide compound includes trioctylamine N-oxide, dilaurylmethylamine N-oxide, lauryldimethylamine N-oxide, stearyldimethylamine N-oxide, tricaprylamine N-oxide, tridecylamine N-oxide, dimethyldodecylamine N-oxide, trihexylamine N-oxide, tridecylamine N-oxide, benzyldimethylamine N-oxide and benzyldiethylamine N-oxide. These amine N-oxide compounds may be prepared by adding the corresponding amine compound to a reaction system and then reacting the compound with hydrogen peroxide in the reaction system.

The quaternary phosphonium salt includes tetrabutylphosphonium bromide. The crown ether compound includes 12-crown-4,18-crown-6 and benzo-18-crown-6. The polyethylene glycol compound includes polyethylene glycol 600 (average molecular weight: 600), polyethylene glycol 700 (average molecular weight: 700) and polyethylene glycol 800 (average molecular weight: 800).

The amount used of such a phase transfer catalyst may be a catalytic amount and it is usually 0.0005 mol or more per 1 mol of the arylhydrazine compound. There is no upper limit in particular, but in view of economy, the amount is 1 mol or less per 1 mol of the arylhydrazine compound.

After completion of the reaction, the reaction solution as it is or, if necessary, after remaining hydrogen peroxide is degraded with a reducing agent such as sodium thiosulfate may be subjected to concentration, crystallization or the like to isolate the desired biaryl compound. Alternatively, after water and/or a water-insoluble organic solvent is added to the reaction solution if necessary, the reaction solution may be extracted to obtain an organic layer and the organic layer may be concentrated to isolate the biaryl compound. The isolated biaryl compound may be further purified by distillation or a conventional purification means such as column chromatography.

The water-insoluble organic solvent includes aromatic hydrocarbon solvents such as toluene or xylene, halogenated hydrocarbon solvents such as dichloromethane, chloroform or chlorobenzene, ether solvents such as diethyl ether, methyl tert-butyl ether or tetrahydrofran and ester solvents such as ethyl acetate, and the amount used is not particularly limited.

The desired biaryl compound can be obtained by reaction between the arylhydrazine compound, hydrogen peroxide and the aryl compound. The desired biaryl compound can be produced in a further better yield by performing such reaction in the presence of at least one species selected from the group consisting of the aforementioned groups (A) and (B).

The Group Va element metal or the compound thereof includes vanadium metal, vanadium compounds such as vanadium oxide, ammonium vanadate or a vanadium carbonyl complex, niobium metal, and niobium compounds such as niobium oxide, niobium chloride or a niobium carbonyl complex. The Group VIa element metal or the compound thereof includes tungsten metal, tungsten compounds such as tungsten boride, tungsten carbide, tungsten oxide, ammonium tungstate or a tungsten carbonyl complex, molybdenum metal, and molybdenum compounds such as molybdenum boride, molybdenum oxide, molybdenum chloride or a molybdenum carbonyl complex.

The Group VIIa element metal or the compound thereof includes rhenium metal, rhenium compounds such as rhenium oxide, a complex of rhenium oxide, rhenium chloride, or alkylrhenium trioxide such as methylrhenium trioxide. The Group VIIIa element metal or the compound thereof includes cobalt metal, and cobalt compounds such as cobalt oxide, a complex of cobalt oxide or cobalt chloride.

The Group Va element oxide obtained by reacting the Group Va element metal or a compound thereof with hydrogen peroxide includes vanadium oxide obtained by reacting the aforementioned vanadium compound with hydrogen oxide, and niobium oxide obtained by reacting the aforementioned niobium compound with hydrogen peroxide. The Group VIa element oxide obtained by reacting a Group VIa element metal or a compound thereof with hydrogen peroxide includes tungsten oxide obtained by reacting the aforementioned tungsten metal or tungsten compound with hydrogen peroxide, and the molybdenum oxide obtained by reacting the aforementioned molybdenum metal or molybdenum compound with hydrogen peroxide.

The Group VIIa element oxide obtained by reacting the Group VIIa element metal or a compound thereof with hydrogen peroxide includes rhenium oxide obtained by reacting the aforementioned rhenium compound with hydrogen oxide. The Group. VIIIa element oxide obtained by reacting the Group VIIIa element metal or the compound thereof with hydrogen peroxide includes cobalt oxide obtained by reacting the aforementioned cobalt compound with hydrogen peroxide.

Among such metals and metal compounds, tungsten metal, tungsten compounds, cobalt compounds, niobium compounds, molybdenum metal, molybdenum compounds, rhenium compounds, tungsten oxide, cobalt oxide, niobium oxide, molybdenum oxide and a mixture thereof are preferable. Such metals and metal compounds may be used alone or as a mixture thereof.

Hydrogen peroxide which is used in producing the compounds of the group (B) (hereinafter, also referred to as metal oxide) is usually in a form of an aqueous solution. Of course, a solution of hydrogen peroxide in an organic solvent may be used, but from a viewpoint of easy handling, it is preferable to use the solution of hydrogen peroxide in water. The hydrogen peroxide concentration in the solution of hydrogen peroxide in water or an organic solvent is not particularly limited, but in view of volume efficiency and safety, it is practically 1 to 60% by weight. When the solution of hydrogen peroxide in water is used, a commercially available hydrogen peroxide solution may be used as it is or, if necessary, after adjusting the concentration by dilution or concentration. When the solution of hydrogen peroxide in an organic solvent is used, the solution prepared, for example, by extracting the solution of hydrogen peroxide in water with an organic solvent or by distilling the solution of hydrogen peroxide in water in the presence of an organic solvent may be used.

The amount used of hydrogen peroxide in producing the compounds of the group (B) is usually 3 mol or more, preferably 5 mol or more per 1 mol of the Group Va element metal or a compound thereof, the Group VIa element metal or a compound thereof, the Group VIIa element metal or a compound thereof, or the Group VIIIa element metal or a compound thereof. There is no upper limit in particular.

Preparation of the metal oxide is usually performed in an aqueous solution. Of course, the preparation may be performed in an organic solvent such as an ether solvent such as diethyl ether, methyl tert-butyl ether or tetrahydrofran, an ester solvent such as ethyl acetate or a nitrile solvent such as acetonitrile or propionitrile, or a mixture of the organic solvent and water.

Preparation of the metal oxide is performed by mixing and contacting a metal or a metal compound of the group (A) with hydrogen peroxide and, in order to increase contact efficiency, such reaction is preferably performed with stirring so as to sufficiently disperse a metal or a metal compound of the group. (A) in a solution for preparing metal oxide. In addition, in order to increase the contact efficiency between a metal or a metal compound of the group (A) and hydrogen peroxide and control preparation of the metal oxide more easily, for example, a metal or a metal compound of the group (A) in powder form is preferably used.

The temperature in preparation of metal oxide is usually −10 to 100° C.

A metal or a metal compound of the group (A) and hydrogen peroxide can be reacted in water, an organic solvent or a mixture of an organic solvent and water to dissolve all or a part of the metal or metal compound of the group (A) and thereby prepare a homogeneous solution or suspension containing metal oxide. The metal oxide may be isolated from a preparation solution, for example, by concentration and then may be used as a catalyst, or the preparation solution may be used as it is as the catalyst. When the preparation solution is used as it is as the catalyst, the amount used of hydrogen oxide in the reaction of the arylhydrazine compound, hydrogen peroxide and the aryl compound may be determined in view of the content of hydrogen peroxide in the preparation solution.

Alternatively, preparation of the metal oxide and reaction between the arylhydrazine compound, hydrogen peroxide and the aryl compound may be performed simultaneously by contacting and mixing each metal or the metal compound of the group (A), the arylhydrazine compound, hydrogen peroxide and the aryl compound.

The amount used of each metal or the metal compound of the group (A) is usually 0.001 mol or more per 1 mol of the arylhydrazine compound. There is no upper limit of the amount in particular, but in view of economy, it is practically 1 mol or less per 1 mol of the arylhydrazine compound.

In the reaction using the metal or a compound of the group (A), like the reaction without it, it is preferable that the reaction is performed while removing water present in the reaction system or the reaction is performed in the presence of a phase transfer catalyst.

The phase transfer catalyst and the amount used thereof are as described above. Such a phase transfer catalyst may be also previously used in preparation of the aforementioned metal oxide catalyst.

When the arylhydrazine compound, hydrogen peroxide and the aryl compound are reacted in the presence of the metal compound and the desired biaryl compound is isolated by extraction or crystallization, the metal compound catalyst is contained in an aqueous layer obtained by extraction of the reaction solution or in a filtrate obtained by crystallization from the reaction solution. Thus, the aqueous layer or the filtrate can be used in the present reaction again as it is or after concentration if necessary.

The biaryl compound thus obtained includes a biaryl compound represented by the formula (3):

Ar—Ar' (3)

wherein Ar and Ar' are as defined above, and a 2-arylbenzothiazole compound represented by the formula (3'):

(3')

wherein Ar' is as defined above and X has the same meaning as that of the substituent of Ar, which is included in the biaryl compound of the formula (3).

Specific examples of the biaryl compound include biphenyl, 2-fluorobiphenyl, 3-fluorobiphenyl, 4-fluorobiphenyl, 2-chlorobiphenyl, 3-chlorobiphenyl, 4-chlorobiphenyl, 2-bromobiphenyl, 3-bromobiphenyl, 4-bromobiphenyl, 2-phenyltoluene, 3-phenyltoluene, 4-biphenyltoluene, 2-methoxybiphenyl, 3-cyanobiphenyl, 4-carbomethoxybiphenyl, 2-carbomethoxybiphenyl, 2-phenylbenzoic acid, 2-n-butoxycarbonylbiphenyl, 4-nitrobiphenyl, 2-trifluoromethylbiphenyl, 3-trifluoromethylbiphenyl, 4-trifluoromethylbiphenylhydrazine, 2-sulfobiphenyl, 4-sulfonamidobiphenyl, ethyl 4-sulfonate biphenyl, 3-methylsulfonbiphenyl, 2,4-dinitrobiphenyl, 2,4-dichlorobiphenyl, 2,4-difluorobiphenyl, 3,5-difluorobiphenyl, 3,5-di(trifluoromethyl)biphenyl, 3-chloro-4-fluorobiphenyl, 2-carboxy-3-chlorobiphenyl, 2-methoxycarbonyl-3-chlorobiphenyl, 3-sulfonamido-2-acetylaminobiphenyl, 2,3,5-trichlorobiphenyl, 2,4-difluoro-5-nitrobiphenyl, 2,3,5,6-tetrafluorobiphenyl, 2,3,4,5,6-pentafluorobiphenyl, 2-benzylbiphenyl, 3-benzyloxybiphenyl, 4-benzyloxybiphenyl, 4-phenyl-1,8-naphthalic acid anhydride, diethyl 2-methyl-2-((3'-fluoro-4'-phenyl)phenyl)malonate, 4-chloro-3-hydroxy-2-fluorobiphenyl, 4-trifluoromethyl-2,6-dichlorobiphenyl, 5-methoxy-2,4-dichlorobiphenyl, 6-bromo-2-phenylpyridine, 2-phenylpyrimidine, 4-trifluoromethyl-2-phenylpyrimidine, 2-ethoxy-4-fluoro-6-phenylpyrimidine, 2,4-dimethoxy-6-phenylquinoline, 2-phenylquinoline, 4-nitro-2-phenylquinoline, 3-tert-butyl-2-cyanobiphenyl, 4-(2',5'-dicarbomethoxyphenyl)-trifluoromethylbenzene, 3-phenylphenol, 2-aminobiphenyl, 4-biphenylacetic acid, 4-methyl-2-(methoxymethylcarbonyl)biphenyl, 4-methyl-3-(methoxymethylcarbonyl)biphenyl, 4-methyl-3-(chloromethyl)biphenyl, 4-methyl-3-cyanobiphenyl, 4-methyl-2',6'-dimethoxybiphenyl, 2,2'-difluorobiphenyl, 3,3'-dichlorobiphenyl, 4,4'-dibromobiphenyl, 3,5-dinitrobiphenyl, 3,5-dinitrophenyltoluene, 2,4'-chlorofluorobiphenyl, 2-phenylpyridine, 3-phenylpyridine, 4-phenylpyridine, 2,2'-bipyridyl, 3,3'-bipyridyl, 4,4'-bipyridyl, 1-phenylnaphthalene, 1,1'-binaphthyl, 2-phenylbenzothiazole, 2-phenylbenzoxazole, 2-(2-methylphenyl)benzothiazole, 2-(3-methylphenyl)benzothiazole, 2-(4-methylphenyl)benzothiazole, 2-(3-methyl-4-methoxyphenyl)benzothiazole, 2-(2-chlorophenyl) benzothiazole, 2-(2-fluorophenyl)benzothiazole, 2-(2,4-dichlorophenyl)benzothiazole, 2-(2,5-dichlorophenyl) benzoxazole, 2-(2,5-dimethylphenyl)benzothiazole, 2-(2,5-difluorophenyl)benzothiazole, 2-(4-nitrophenyl) benzothiazole, 2-(2-pyridyl)benzothiazole, 2-phenyl-4-methylbenzothiazole, 2-phenyl-5-methylbenzoxazole, 2-phenyl-6-methylbenzothiazole, 2-phenyl-7-methylbenzothiazole, 2-phenyl-4-ethylbenzoxazole, 2-phenyl-5-isopropylbenzothiazole, 2-phenyl-4-methoxybenzothiazole, 2-(4-methoxyphenyl)-5-methoxybenzothiazole, 2-phenyl-6-methoxybenzothiazole, 2-phenyl-7-methoxybenzoxazole, 2-(4-methoxyphenyl)-5,7-dimethoxybenzothiazole, 2-phenyl-4,6-dimethoxybenzothiazole, 2-phenyl-5,6-dimethoxybenzoxazole, 2-phenyl-4-ethoxybenzothiazole, 2-phenyl-5-benzyloxybenzothiazole, 2-phenyl-7-benzyloxybenzothiazole, 2-phenyl-4-chlorobenzothiazole, 2-phenyl-5-chlorobenzoxazole, 2-phenyl-6-chlorobenzothiazole, 2-phenyl-4-fluorobenzothiazole, 2-phenyl-5-fluorobenzoxazole, 2-phenyl-6-fluorobenzothiazole, 2-(3-methylphenyl)-6-fluorobenzothiazole, 2-(3-methyl-4-nitrophenyl)-6-fluorobenzothiazole, 2-phenyl-5,7-dichlorobenzothiazole, 2-phenyl-4,6-dichlorobenzoxazole, 2-phenyl-5,6-dichlorobenzothiazole, 2-phenyl-5,7-difluorobenzoxazole, 2-phenyl-4,6-difluorobenzothiazole, 2-phenyl-5,6-difluorobenzothiazole, 2-phenyl-5-(2-carbomethoxyethyl)benzothiazole, 2-phenyl-6-bromobenzoxazole, 2-phenyl-5-trifluoromethylbenzothiazole, 2-phenyl-6-trifluoromethylbenzoxazole, 2-phenyl-5-cyanobenzothiazole, 2-phenyl-6-cyanobenzoxazole, 2-phenyl-5-nitrobenzothiazole and 2-phenyl-6-nitrobenzothiazole.

Then, the process for producing a biaryl compound which comprises reacting the arylhydrazine compound and hydrogen peroxide in the presence of at least one species selected from the group consisting of groups (A) and (B) will be explained.

By reacting the arylhydrazine compound and hydrogen peroxide, a biaryl compound in which two molecules of an arylhydrazine compound are self-coupled is obtained. For example, when phenylhydrazine is used as the arylhydrazine compound, biphenyl is obtained.

The arylhydrazine compound includes the same compounds as those described above, for example, the arylhydrazine compound of the formula (1). Hydrogen peroxide includes the same hydrogen peroxides as those described above.

The amount used of hydrogen peroxide is usually 1 mol or more per 1 mol of the arylhydrazine compound and there is no upper limit in particular.

The reaction between the arylhydrazine compound and hydrogen peroxide is usually performed in a solvent which is inert to the reaction. Such solvent includes ether solvents such as diethyl ether, methyl tert-butyl ether or tetrahydrofuran, ester solvents such as ethyl acetate, nitrile solvents such as acetonitrile or propionitrile, and aliphatic hydrocarbon solvents such as cyclohexane or n-heptane. The amount used of such solvent is not particularly limited, but in view of volume efficiency, it is practically 100 parts by weight or less per 1 part by weight of the arylhydrazine compound.

If the reaction temperature is too low, the reaction hardly proceeds and, if the reaction temperature is too high, side reaction such as degradation of the starting material arylhydrazine compound and the produced biaryl compound may proceed. Therefore, the practical reaction temperature is in a range of 0° C. to 200° C.

The reaction is usually performed by contacting and mixing the arylhydrazine compound with hydrogen peroxide, and the order of mixing them is not limited.

The reaction between the arylhydrazine compound and hydrogen peroxide may be performed under normal pressure or under pressurized pressure. In addition, progression of the reaction can be confirmed by a conventional analysis means such as gas chromatography, high performance liquid chromatography, thin layer chromatography, NMR and IR.

Since water is produced as a by-product in this reaction as the reaction proceeds, like the aforementioned reaction between the arylhydrazine compound, hydrogen peroxide and the aryl compound, it is preferable to perform the reaction while removing water present in the reaction system or perform the reaction in the presence of a phase transfer catalyst. Examples of a method of performing the reaction while removing water present in the reaction system are the same as the described above. Examples of the phase transfer catalyst are also the same as described above.

After completion of the reaction, the reaction solution as it is or, if necessary, after remaining hydrogen peroxide is degraded with a reducing agent such as sodium thiosulfate may be subjected to concentration, crystallization or the like to isolate the desired biaryl compound. Alternatively, after water and/or a water-insoluble organic solvent is added to the reaction solution if necessary, the reaction solution may be extracted to obtain an organic layer and the organic layer may be concentrated to isolate a biaryl compound. The isolated biaryl compound may be further purified by distillation or a conventional purification means such as column chromatography.

Examples of the water-insoluble organic solvent are the same as described above, and its amount used is not particularly limited.

The desired biaryl compound can be obtained by reacting the arylhydrazine compound with hydrogen peroxide and the biaryl compound can be produced in a further better yield by performing such reaction in the presence of at least one catalyst selected from the group consisting of the groups (A) and (B) (hereinafter, abbreviated as the metal compound).

Examples of the metal compound are the same as described above. Its amount used may be a catalytic amount, and it is usually 0.001 mol or more per 1 mol of the arylhydrazine compound. There is no upper limit of the amount in particular, but in view of economy, it is practically 1 mol or less per 1 mol of the arylhydrazine compound.

In the reaction using the metal compound, like the reaction without it, it is preferable that the reaction is performed while removing water present in the reaction system or the reaction is performed in the presence of a phase transfer catalyst.

Examples of the phase transfer catalyst are the same as described above. Its use amount is also as described above. Such a phase transfer catalyst may be previously used in preparation of the aforementioned metal oxide catalyst.

When the arylhydrazine compound and hydrogen peroxide are reacted in the presence of the metal compound and the desired biaryl compound is isolated by extraction or crystallization, the metal compound catalyst is contained in an aqueous layer obtained by extraction of the reaction solution or in a filtrate obtained by crystallization from the reaction solution. Thus, the aqueous layer or the filtrate can be used in the present reaction again as it is or after concentration if necessary.

The biaryl compound thus obtained includes a biaryl compound represented by the formula (4):

Ar—Ar            (4)

wherein Ar is as defined above, and specific examples thereof include biphenyl, 2,2'-difluorobiphenyl, 3,3'-dichlorobiphenyl, 4,4'-dibromobiphenyl, 2,2'-bipyridyl, 3,3'-bipyridyl, 4,4'-bipyridyl and 1,1'-binaphthyl.

EXAMPLES

The following Examples further illustrate the present invention in detail, but the present invention is not limited by these Examples.

Example 1

Into a 50 mL flask, toluene (15 g) and anhydrous magnesium sulfate (3 g) were charged and 30% by weight hydrogen peroxide solution in water (1100 mg) was added dropwise over 5 minutes thereto. Then, the inner temperature of the mixture was increased to 80° C. A mixture of phenylhydrazine (220 mg) and toluene (15 g) was added dropwise at the same temperature over 1 hour into the flask and the mixture was stirred and retained for another 1 hour to be reacted. After cooled to room temperature, water (10 g) was added, and the mixture was stirred and then allowed to stand at room temperature to separate layers. The obtained organic layer containing phenyltoluene was analyzed by gas chromatography. As a result, the yield of phenyltoluene was found to be 27% and the isomer ratio was found to be o-isomer:m-isomer:p-isomer=61:23:16.

Example 2

Into a 50 mL flask, toluene (15 g), 30% by weight hydrogen peroxide solution in water (1350 mg) and trimethyloctylammonium hydrogen sulfate salt (60 mg) were charged and the inner temperature of the mixture was increased to 80° C. A mixture of phenylhydrazine (220 mg) and toluene (5 g) was added dropwise at the same temperature over 3 hours into the flask and the mixture was stirred and retained for another 1 hour to be reacted. After cooled to room temperature, water (10 g) was added, and the mixture was stirred and then allowed to stand at room temperature to separate layers. The obtained organic layer containing phenyltoluene was analyzed by gas chromatography. As a result, the yield of phenyltoluene was found to be 27% and the isomer ratio was found to be o-isomer:m-isomer:p-isomer=63:22:15.

Example 3

Into a 50 mL flask, toluene (15 g) and 30% by weight hydrogen peroxide solution in water (1350 mg) were charged and the inner temperature of the mixture was increased to 80° C. A mixture of phenylhydrazine (220 mg) and toluene (5 g) was added dropwise at the same temperature over 3 hours into the flask and the mixture was stirred and retained for another 1 hour to be reacted. After cooled to room temperature, water (10 g) was added, and the mixture was stirred and then allowed to stand at room temperature to separate layers. The obtained organic layer containing phenyltoluene was analyzed by gas chromatography. As a result, the yield of phenyltoluene was found to be 16.3% and the isomer ratio was found to be o-isomer: m-isomer:p-isomer=60:22:18.

Example 4

Into a 100 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and benzene (15 g) and anhydrous magnesium sulfate (3 g) were added thereto. Then, 30% by weight hydrogen peroxide solution in water (1100 mg) was added dropwise over 5 minutes. After the inner temperature of the mixture was increased to 80° C., a mixture of 4-methylphenylhydrazine (250 mg) and benzene (15 g) was added dropwise over 1 hour and the mixture was then stirred and retained at the same temperature for another 1 hour to be reacted. After cooled to room temperature, water (10 g) was added, and the mixture was stirred and then allowed to stand to separate layers. The obtained organic layer containing 4-phenyltoluene was analyzed by gas chromatography. As a result, the yield of 4-phenyltoluene was found to be 40%.

Example 5

Into a 100 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and benzene (15 g) and trimethyloctylammonium hydrogen sulfate salt (60 mg) were added thereto. Then, 30% by weight hydrogen peroxide solution in water (1100 mg) was added dropwise over 5 minutes. After the inner temperature of the mixture was increased to 80° C., a mixture of 4-chlorophenylhydrazine (285 mg) and benzene (15 g) was added dropwise over 1 hour and the mixture was then stirred and retained at the same temperature for another 1 hour to be reacted. After cooled to room temperature, water (10 g) was added, and the mixture was stirred and then allowed to stand to separate layers. The obtained organic layer containing 4-chlorobiphenyl was analyzed by gas chromatography. As a result, the yield of 4-chlorobiphenyl was found to be 82%.

Example 6

In the same manner as that of Example 5 except that 2-fluorophenylhydrazine (252 mg) was used in place of 4-chlorophenylhydrazine (285 mg), an organic layer containing 2-fluorobiphenyl was obtained. The organic layer was analyzed by gas chromatography and as a result, the yield of 2-fluorobiphenyl was found to be 80%.

Example 7

Into a 100 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and benzene (15 g) and trimethyloctylammonium hydrogen sulfate salt (60 mg) were added thereto. Then, 30% by weight hydrogen peroxide solution in water (1100 mg) was added dropwise over 5 minutes. After the inner temperature of the mixture was increased to 80° C., a mixture of 4-nitrophenylhydrazine (306 mg) and ethyl acetate (10 g) was added dropwise over 1 hour and the mixture was then stirred and retained at the same temperature for another 1 hour to be reacted. After cooled to room temperature, water (10 g) was added, and the mixture was stirred and then allowed to stand to separate layers. The obtained organic layer containing 4-nitrobiphenyl was analyzed by gas chromatography. As a result, the yield of 4-nitrobiphenyl was found to be 67%.

Example 8

Into a 100 mL flask, tungsten metal (200 mg) and 30% by weight hydrogen peroxide solution in water (1.0 g) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and benzene (40 g) and trimethyloctylammonium hydrogen sulfate salt (300 mg) were added thereto. Then, 30% by weight hydrogen peroxide solution in water (11.0 g) was added dropwise over 5 minutes. After the inner temperature of the mixture was increased to 80° C., a mixture of 2,4-difluorophenylhydrazine (2.88 g) and benzene (10 g) was added dropwise over 3 hours and the mixture was then stirred and retained at the same temperature for another 1 hour to be reacted. After cooled to room temperature, water (20 g) was added, and the mixture was stirred and then allowed to stand to separate layers. The obtained organic layer containing 2,4-difluorobiphenyl was analyzed by gas chromatography. As a result, the yield of 2,4-difluorobiphenyl was found to be 90%. From this solution, the solvent was distilled off to obtain a yellow crystal (3.5 g). The purity of the crystal was found to be 97.5% (GC area percentage).

Example 9

Into a 200 mL flask, tungsten metal (400 mg) and water (2 g) was added and warmed to 40° C. with stirring. Then, 30% by weight hydrogen peroxide solution in water (2.5 g) was added dropwise over 30 minutes and the mixture was stirred and retained at the same temperature for 0.5 hours to prepare an aqueous solution of tungsten metal oxide. The inner temperature of the aqueous solution was adjusted to 30° C. and benzene (90 g) and trimethyloctylammonium hydrogen sulfate salt (600 mg) were added thereto. Then, 30% by weight hydrogen peroxide solution in water (33.0 g) was added dropwise over 5 minutes. After the inner temperature of the mixture was increased to 80° C., a mixture of 4-fluorophenylhydrazine (7.56 g) and benzene (20 g) was added dropwise over 5 hours and the mixture was then stirred and retained at the same temperature for another 1 hour to be reacted. After cooled to room temperature, water (20 g×2) was added and the mixture was stirred and then allowed to stand to separate layers. The obtained organic layer containing 4-fluorobiphenyl was analyzed by gas chromatography. As a result, the yield of 4-fluorobiphenyl was found to be 90%. From this solution, the solvent was distilled off to obtain a yellow crystal (7.5 g). The purity of the crystal was found to be 97.0% (GC area percentage).

Example 10

Into a 100 mL flask, tungsten metal (200 mg) and 30% by weight hydrogen peroxide solution in water (1.0 g) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and benzene (40 g) and trimethyloctylammonium hydrogen sulfate salt (300 mg) were added thereto. Then, 30% by weight hydrogen peroxide solution in water (11.0 g) was added dropwise over 5 minutes. After the inner temperature of the mixture was increased to 80° C., a mixture of diethyl 2-methyl-2-((3'-fluoro-4'-hydrazino)phenyl)malonate (1.0 g) and benzene (10 g) was added dropwise over 3 hours and the mixture was then stirred and retained at the same temperature for another 1 hour to be reacted. After cooled to room temperature, water (20 g) was added, and the mixture was stirred and then allowed to stand to separate layers. The obtained organic layer containing diethyl 2-methyl-2-((3'-fluoro-4'-phenyl)phenyl)malonate was analyzed by gas chromatography. As a result, the yield of diethyl 2-methyl-2-((3'-fluoro-4'-phenyl)phenyl)malonate was found to be 0.80%.

Example 11

In the same manner as that of Example 5 except that 3-cyanophenylhydrazine (266 mg) was used in place of 4-chlorophenylhydrazine (285 mg), an organic layer containing 3-cyanobiphenyl was obtained. The organic layer was analyzed by gas chromatography and as a result, the yield of 3-cyanobiphenyl was found to be 85%.

Example 12

In the same manner as that of Example 5 except that 4-trifluoromethylphenylhydrazine (353 mg) was used in place of 4-chlorophenylhydrazine (285 mg), an organic layer containing 4-trifluoromethylbiphenyl was obtained. The organic layer was analyzed by gas chromatography and as a result, the yield of 4-trifluoromethylbiphenyl was found to be 88%.

Example 13

In the same manner as that of Example 7 except that 2-carbobutoxyphenylhydrazine (306 mg) was used in place of 4-nitrophenylhydrazine (306 mg), an organic layer containing 2-carbobutoxybiphenyl was obtained. The organic layer was analyzed by gas chromatography and as a result, the yield of 2-carbobutoxybiphenyl was found to be 30%.

Example 14

In the same manner as that of Example 7 except that 2-hydrazino-6-bromopyridine (120 mg) was used in place of 4-nitrophenylhydrazine (306 mg), an organic layer containing 2-phenyl-6-bromopyridine was obtained. The organic layer was analyzed by gas chromatography and as a result, the yield of 2-phenyl-6-bromopyridine was found to be 42%.

Example 15

In the same manner as that of Example 7 except that 2-hydrazino-4-trifluoromethylpiperazine (360 mg) was used in place of 4-nitrophenylhydrazine (306 mg), an organic layer containing 2-phenyl-4-trifluoromethylpiperazine was obtained. The organic layer was analyzed by gas chromatography and as a result, the yield of 2-phenyl-4-trifluoromethylpiperazine was found to be 26%.

Example 16

Into a 100 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and 4-tert-butylcyanobenzene (10 g) and trimethyloctylammonium hydrogen sulfate salt (60 mg) were added thereto. Then, 30% by weight hydrogen peroxide solution in water (1100 mg) was added dropwise over 5 minutes. After the inner temperature of the mixture was increased to 80° C., a mixture of phenylhydrazine (216 mg) and ethyl acetate (5 g) was added dropwise over 2 hours and the mixture was then stirred and retained at the same temperature for another 1 hour to be reacted. After cooled to room temperature, water (10 g) was added, and the mixture was stirred and then allowed to stand to separate layers. The obtained organic layer containing 3-tert-butyl-2-cyanobiphenyl was analyzed by gas chromatography. As a result, the yield of 3-tert-butyl-2-cyanobiphenyl was found to be 25%.

Example 17

Into a 100 mL flask, tungsten metal (60 mg) and 30% by weight hydrogen peroxide solution in water (400 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was adjusted to 30° C. and dimethyl terephthalate (15 g), ethyl acetate (15 g) and trimethyloctylammonium hydrogen sulfate salt (60 mg) were added thereto. Then, 30% by weight hydrogen peroxide solution in water (3.3 g) was added dropwise over 5 minutes. After the inner temperature of the mixture was increased to 80° C., a mixture of 4-trifluoromethylphenylhydrazine (1.0 g) and ethyl acetate (15 g) was added dropwise over 2 hours and the mixture was then stirred and retained at the same temperature for another 1 hour to be reacted. After cooled to room temperature, water (10 g) was added, and the mixture was stirred and then allowed to stand to separate layers. The obtained organic layer containing 4-(2',5'-dicarbomethoxyphenyl)-trifluoromethylbenzene was analyzed by gas chromatography. As a result, the yield of 4-(2',5'-dicarbomethoxyphenyl)-trifluoromethylbenzene was found to be 30%.

Example 18

Into a 50 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was cooled to 30° C. and toluene (15 g), 30% by weight hydrogen peroxide solution in water (1100 mg) and trimethyloctylammonium hydrogen sulfate salt (60 mg) were added thereto. After the inner temperature of the mixture was increased to 50° C., a mixture of phenylhydrazine (220 mg) and toluene (5 g) was added dropwise at the same temperature over 1 hour and the mixture was then stirred and retained for another 1 hour to be reacted. After cooled to room temperature, water (10 g) was added, and the mixture was stirred and then allowed to stand at room temperature to separate layers. The obtained organic layer containing phenyltoluene was analyzed by gas chromatography.

As a result, the yield of phenyltoluene was found to be 39% and the isomer ratio was found to be o-isomer: m-isomer:p-isomer=65.4:20.4:14.2.

Example 19

Into a 50 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was cooled to 30° C. and toluene (15 g), 30% by weight hydrogen peroxide solution in water (1100 mg) and dimethyldodecylamine N-oxide (60 mg) were added thereto. After the inner temperature of the mixture was increased to 60° C., a mixture of phenylhydrazine (220 mg) and toluene (5 g) was added dropwise at the same temperature over 3 hours and the mixture was then stirred and retained for another 1 hour to be reacted. After cooled to room temperature, water (10 g) was added, and the mixture was stirred and then allowed to stand at room temperature to separate layers. The obtained organic layer containing phenyltoluene was analyzed by gas chromatography. As a result, the yield of phenyltoluene was found to be 35% and the isomer ratio was found to be o-isomer: m-isomer: p-isomer=62:24:14.

Example 20

Into a 50 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was cooled to 30° C. and toluene (15 g) and anhydrous magnesium sulfate (3 g) were added. After 30% by weight hydrogen peroxide solution in water (1100 mg) was added dropwise over 5 minutes, the inner temperature of the mixture was increased to 80° C. A mixture of phenylhydrazine (220 mg) and toluene (15 g) was added dropwise at the same temperature over 1 hour and the mixture was then stirred and retained for another 1 hour to be reacted. After cooled to room temperature, water (10 g) was added, and the mixture was stirred and then allowed to stand at room temperature to separate layers. The obtained organic layer containing phenyltoluene was analyzed by gas chromatography. As a result, the yield of phenyltoluene was found to be 40% and the isomer ratio was found to be o-isomer: m-isomer:p-isomer=64:21:15.

Example 21

In the same manner as that of Example 20 except that cobalt oxide (12 mg) was used in place of tungsten metal (40 mg), an organic layer containing phenyltoluene was obtained. The yield of phenyltoluene was found to be 31%, and the isomer ratio was found to be o-isomer: m-isomer:p-isomer=64:21:15.

Example 22

In the same manner as that of Example 20 except that niobium metal (20 mg) was used in place of tungsten metal (40 mg), an organic layer containing phenyltoluene was obtained. The yield of phenyltoluene was found to be 32% and the isomer ratio was found to be o-isomer: m-isomer:p-isomer=64:21:15.

Example 23

In the same manner as that of Example 18 except that molybdenum metal (20 mg) was used in place of tungsten metal, phenyltoluene was obtained. The yield of phenyltoluene was found to be 30% and the isomer ratio was found to be o-isomer: m-isomer:p-isomer=63:23:14.

Example 24

In the same manner as that of Example 20 except that methylrhenium trioxide is used in place of tungsten metal, phenyltoluene is obtained.

Example 25

Into a 50 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was cooled to 30° C. and chlorobenzene (15 g) and anhydrous magnesium sulfate (3 g) were added. After 60% by weight hydrogen peroxide solution in water (900 mg) was added dropwise over 5 minutes, the inner temperature of the mixture was increased to 80° C. A mixture of phenylhydrazine (220 mg) and chlorobenzene (15 g) was added dropwise at the same temperature over 1 hour and the mixture was then stirred and retained for another 1 hour to be reacted. After cooled to room temperature, water (10 g) was added, and the mixture was stirred and then allowed to stand at room temperature to separate layers. The obtained organic layer containing chlorobiphenyl was analyzed by gas chromatography. As a result, the yield of chlorobiphenyl was found to be 39% and the isomer ratio was found to be o-isomer: m-isomer:p-isomer=62:20:18.

Example 26

Into a 50 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was cooled to 30° C. and pyridine (10 g) and anhydrous magnesium sulfate (3 g) were added. After 60% by weight hydrogen peroxide solution in water (900 mg) was added dropwise over 5 minutes, the inner temperature of the mixture was increased to 80° C. A mixture of phenylhydrazine (220 mg) and pyridine (8 g) was added dropwise at the same temperature over 1 hour and the mixture was then stirred and retained for another 1 hour to be reacted. After cooled to room temperature, water (10 g) was added, and the mixture was stirred and then allowed to stand at room temperature to separate layers. The obtained organic layer containing phenylpyridine was analyzed by gas chromatography. As a result, the yield of phenylpyridine was found to be 27% and the isomer ratio was found to be o-isomer: m-isomer:p-isomer=47:28:25.

Example 27

Into a 50 mL flask, tungsten metal (40 mg) and 30% by weight hydrogen peroxide solution in water (250 mg) were charged and the inner temperature of the mixture was increased to 40° C. The mixture was stirred and retained at the same temperature for 0.5 hours to prepare an aqueous solution of tungsten metal oxide. The inner temperature of the aqueous solution was cooled to 30° C. and toluene (15 g), 30% by weight hydrogen peroxide solution in water (1100 mg) and trimethyloctylammonium hydrogen sulfate salt (60 mg) were added. After the inner temperature of the mixture was increased to 80° C., a mixture of 3,5-dinitrophenylhydrazine (400 mg) and toluene (5 g) was added dropwise at the same temperature over 1 hour and the mixture was then stirred and retained for another 1 hour to be reacted. After cooled to room temperature, water (10 g) was added, and the mixture was stirred and then allowed to stand at room temperature to separate layers. The obtained organic layer containing 3,5-dinitrophenyltoluene was analyzed by gas chromatography. As a result, the yield of 3,5-dinitrophenyltoluene (a mixture of three isomers) was found to be 70%.

Example 28

Into a 50 mL flask, acetonitrile (10 g) and anhydrous magnesium sulfate (3 g) were charged and 30% by weight hydrogen peroxide solution in water (1100 mg) was added dropwise over 5 minutes. The inner temperature of the mixture was then increased to 80° C. and phenylhydrazine (220 mg) was added dropwise over 5 minutes. The mixture was then stirred and retained at the same temperature for another 1 hour to be reacted. After cooled to room temperature, water (10 g) was added, and the mixture was stirred and then allowed to stand to separate layers. The obtained organic layer containing biphenyl was analyzed by gas chromatography. As a result, the yield of biphenyl was found to be 6%.

Example 29

Into a 50 mL flask, tungsten metal (40 mg) and 30% by weight aqueous hydrogen peroxide solution in water (250 mg) were charged and the inner temperature of the mixture was then increased to 40° C. The mixture was stirred and retained at the same temperature for 0.5 hours to prepare an aqueous solution of tungsten metal oxide. The inner temperature of the aqueous solution was cooled to 30° C. and benzene (15 g), 30% by weight aqueous hydrogen peroxide solution in water (1100 mg) and trimethyloctylammonium hydrogen sulfate salt (60 mg) were added. After the inner temperature of the mixture was increased to 60° C., a mixture of 2-hydrazinobenzothiazole (330 mg) and benzene (5 g) was added dropwise at the same temperature over 1 hour and the mixture was then stirred and retained at the same temperature for another 1 hour to be reacted. After cooled to room temperature, water (10 g) was added, and the mixture was stirred and then allowed to stand to separate layers. An organic layer containing 2-phenylbenzothiazole was obtained and the yield of 2-phenylbenzothiazole was found to be 40%.

Example 30

Into a 50 mL flask, benzene (15 g) and 13% by weight aqueous hydrogen peroxide solution in water (5.8 g) were charged and the inner temperature of the mixture was then increased to 60° C. A mixture of 2-hydrazinobenzothiazole (330 mg) and benzene (5 g) was added dropwise at the same temperature over 1 hour and the mixture was then stirred and retained at the same temperature for another 1 hour to be reacted. After cooled to room temperature, water (10 g) was added, and the mixture was stirred and then allowed to stand to separate layers. An organic layer containing 2-phenylbenzothiazole was obtained and the yield of 2-phenylbenzothiazole was found to be 10%.

Example 31

In the same manner as that of Example 29 except that 2-hydrazinobenzoxazole (306 mg) was used in place of 2-hydrazinobenzothiazole (330 mg), an organic layer containing 2-phenylbenzoxazole was obtained. The yield of 2-phenylbenzoxazole was found to be 23%.

INDUSTRIAL APPLICABILITY

According to the process of the present invention, a biaryl compound can be easily obtained from an arylhydrazine compound, or an arylhydrazine compound and an aryl compound by using hydrogen peroxide, which is inexpensive, easy to use and converted into harmless water after reaction, that is, clean and excellent. Moreover, a biaryl compound can be obtained in a further better yield by performing the reaction in the presence of a Group Va element metal or a compound thereof, a Group VIa element metal or a compound thereof, a Group VIIa element metal or a compound thereof, a Group VIIIa element metal or a compound thereof or the like, such as easily available tungsten metal or molybdenum metal, which is industrially advantageous.

The invention claimed is:

1. A process for producing a biaryl compound, which comprises reacting an arylhydrazine compound, hydrogen peroxide, and an aryl compound at a temperature in the range of 0 to 200° C., in the presence of at least one species selected from the following group (B):
   (B) a Group Va element metal oxide, a Group VIa element metal oxide, a Group VIIa element metal oxide and a Group VIIIa element metal oxide obtained by reacting the metal or the metal compound of the following group (A) with hydrogen peroxide;
   (A) a Group Va element metal or a compound thereof, a Group VIa element metal or a compound thereof, a Group VIIa element metal or a compound thereof, and a Group VIIIa element metal or a compound thereof.

2. The process for producing a biaryl compound according to claim 1, wherein the arylhydrazine compound is represented by the formula (1):

$$Ar-NHNH_2 \qquad (1)$$

wherein Ar represents an unsubstituted aromatic group or an aromatic group substituted with one or more substituents selected from the group consisting of:
   an unsubstituted alkyl group or an alkyl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group ($-SO_3H$), a sulfonamido group, a sulfonic acid (aryl or alkyl) ester group, a sulfonyl group, a cyano group, a hydroxyl group, a nitro group, an amino group and an amido group,
   an unsubstituted alkoxy group or an alkoxy group substituted with one or more substituents selected from the group consisting of a halogen atom, an alkoxy group, an aryloxy group, an aralkyloxy group, an acyl group, an alkoxycarbonyl group, an aryloxycarbonyl group, an aralkyloxycarbonyl group and a carboxyl group,
   an alkoxycarbonyl group, an unsubstituted aryl group or an aryl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an aryloxy group, an aryloxycarbonyl group, an unsubstituted aralkyl group or an aralkyl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group, and an amido group, the aryl compound is represented by the formula (2):

$$Ar' \qquad (2)$$

wherein Ar' is a substituted or unsubstituted aromatic group and has at least one hydrogen atom bound to the aforementioned group, wherein said substituted aromatic group is substituted with one or more substituents selected from the group consisting of:

a halogen atom, an unsubstituted alkyl group or an alkyl group substituted wit one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an unsubstituted alkoxy group or an alkoxy group substituted with one or more substituents selected from the group consisting of a halogen atom, an alkoxy group, an aryloxy group, an aralkyloxy group, an acyl group, an alkoxycarbonyl group, an aryloxycarbonyl group, an aralkyloxycarbonyl group and a carboxyl group, an unsubstituted aryl group or an aryl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an aryloxy group, an unsubstituted aralkyl group or an aralkyl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an aralkyloxy group, an acyl group, a carboalkoxy group, a carboaryloxy group, a carboaralkyloxy group, a carboxyl group, a sulfo group, a cyano group, a hydroxyl group, a nitro group, and an amino group, and the biaryl compound is represented byte formula (3):

$$Ar—Ar' \qquad (3)$$

wherein Ar and Ar' are as defined above.

3. A process for producing a biaryl compound, which comprises reacting an arylhydrazine compound with hydrogen peroxide at a temperature in the range of 0 to 200° C., in the presence of at least one species selected from the following group (B):

(B) a Group Va element metal oxide, a Group VIa element metal oxide, a Group VIIa element metal oxide and a Group VIIIa element metal oxide obtained by reacting the metal or the metal compound of the following group (A) with hydrogen peroxide:

(A) a Group Va element metal or a compound thereof, a Group VIa element metal or a compound thereof, a Group VIIa element metal or a compound thereof, and a Group VIIIa element metal or a compound thereof.

4. The process according to claim 3, wherein the arylhydrazine compound is a compound represented by the formula (1):

$$Ar—NHNH_2 \qquad (1)$$

wherein Ar represents an unsubstituted aromatic group or an aromatic group substituted with one or more substituents selected from the group consisting of:

an unsubstituted alkyl group or an alkyl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an unsubstituted alkoxy group or an alkoxy group substituted with one or more substituents selected from the group consisting of a halogen atom, an alkoxy group, an aryloxy group, an aralkyloxy group, an acyl group, an alkoxycarbonyl group, an aryloxycarbonyl group, an aralkyloxycarbonyl group and a carboxyl group, an alkoxycarbonyl group, an unsubstituted aryl group or an aryl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group (—$SO_3H$), a sulfonamido group, a sulfonic acid (aryl or alkyl) ester group, a sulfonyl group, a cyano group, a hydroxyl group, a nitro group, an amino group and an amido group, an aryloxy group, an aryloxycarbonyl group, an unsubstituted aralkyl group or an aralkyl group substituted with one or more substituents selected from the group consisting of an alkoxy group, an alkoxycarbonyl group, an aryloxy group, an aryloxycarbonyl group, an aralkyl group, an aralkyloxy group, an aralkyloxycarbonyl group, an acyl group, a halogen atom, a carboxyl group, a sulfo group ($—SO_3H$), a sulfonamido group, a sulfonic acid (aryl or alkyl) ester group, a sulfonyl group, a cyano group, a hydroxyl group, a nitro group, an amino group and an amido group, an aralkyloxy group, an aralkyloxycarbonyl group, an acyl group, a halogen atom, a carboxyl group, a sulfo group ($—SO_3H$), a sulfonamido group, a sulfonic acid (aryl or alkyl) ester group, a sulfonyl group, a cyano group, a hydroxyl group, a nitro group, an amino group, and an amido group, and the biaryl compound is a biaryl compound represented by the formula (4):

$$Ar—Ar \qquad (4)$$

wherein Ar is as defined above.

5. The process for producing a biaryl compound according to claim 1 or 3, wherein hydrogen peroxide solution in water is used.

6. The process for producing a biaryl compound according to claim 1 or 3, wherein the reaction is preformed using hydrogen peroxide solution in water and in the presence of a phase transfer catalyst, and wherein the phase transfer catalyst is quaternary ammonium salt or amine N-oxide.

* * * * *